United States Patent [19]
Katsumata et al.

[11] Patent Number: 5,364,775
[45] Date of Patent: Nov. 15, 1994

[54] PROCESS FOR PRODUCING TRANS-L-HYDROXYPROLINE

[75] Inventors: Ryoichi Katsumata, Tokyo; Takashi Ohshiro, Tottori, both of Japan; Haruhiko Yokoi, Ottawa, Canada; Michio Shiomi, Hofu, Japan

[73] Assignee: Kyowa Hakko Kogyo Co., Ltd., Tokyo, Japan

[21] Appl. No.: 972,824

[22] Filed: Nov. 6, 1992

[30] Foreign Application Priority Data

Nov. 13, 1991 [JP] Japan .................................. 3-296944

[51] Int. Cl.⁵ .............................................. C12P 13/24
[52] U.S. Cl. ................................. 435/107; 435/252.1; 435/873; 435/822
[58] Field of Search ...................... 435/107, 273, 252.1

[56] References Cited

PUBLICATIONS

*Bergey's Manual of Systematic Bacteriology* vol. 1 1984 pp. 491, 494.
Singer et al. *J of Bacteriology* 1955 69:303–306.
Bernheim et al. *J of Biol Chem* 1935 110:165–172.
Stumpf et al. *J of Biol Chem* 1944 153:387–399.
Eguchi et al.; Bull. Chem. Soc. Japan, vol. 47(7), 1704–08 (1974).
Kyun Lee et al.; Bull. Chem. Soc. Japan, vol. 46, 2924–2926 (1973).
Ramaswamy et al.; J. Org. Chem., vol. 42, No. 21, 1977, pp. 3440–3443.

*Primary Examiner*—Marian Knode
*Attorney, Agent, or Firm*—White & Case

[57] ABSTRACT

The present invention provides a process for producing trans-L-hydroxyproline, which comprises culturing a microorganism which is capable of decomposing amino acids other than trans-L-hydroxyproline but which is substantially incapable of decomposing trans-L-hydroxyproline in a culture medium containing collagen hydrolyzate, and recovering trans-L-hydroxyproline from the resulting culture.

The process enhances the content of trans-L-hydroxyproline based on the total weight of amino acids contained in collagen hydrolyzate, and enables efficient production of trans-L-hydroxyproline which is useful as a starting material for the synthesis of medicines.

1 Claim, No Drawings

PROCESS FOR PRODUCING TRANS-L-HYDROXYPROLINE

BACKGROUND OF THE INVENTION

The present invention relates to a process for producing trans-L-hydroxyproline. Trans-L-hydroxyproline is a known compound which is useful as a starting material for the synthesis of medicines such as the anti-inflammatory agent N-acetyl-hydroxyproline.

It is known that hydroxyproline can be produced by extraction from proteins such as collagen or by chemical synthesis. Examples of known chemical synthetic methods are synthesis from allyl bromide and diethylacetamidomalonic acid [*Bull. Chem. Soc. Japan*, 46, 2924 (1973)], synthesis from D-glutamic acid [*Bull. Chem. Soc. Japan*, 47, 1704 (1974)] and synthesis from glyoxal and oxaloacetic acid [*J. Org. Chem.*, 42, 3440 (1977)].

However, these chemical synthetic methods are not suitable for industrial application because the yields of the product are low and the product is obtained as a mixture of four isomers. Accordingly, trans-L-hydroxyproline is generally produced by hydrolyzing a protein derived from an animal tissue such as collagen or elastin which contains trans-L-hydroxyproline in a large amount, followed by isolation through extraction. However, the hydrolyzate obtained by such method contains, in addition to trans-L-hydroxyproline, a variety of neutral amino acids such as glycine, L-proline, L-alanine and L-serine. Therefore, multiple purifying steps are required to isolate trans-L-hydroxyproline from these neutral amino acids.

Accordingly, a need exists for a less complex process for producing trans-L-hydroxyproline on an industrial scale. To this end, the present inventors have developed a process for readily purifying and isolating trans-L-hydroxyproline by culturing a microorganism in a culture medium containing a collagen hydrolyzate and decomposing amino acids other than trans-L-hydroxyproline in the culture medium.

SUMMARY OF THE INVENTION

The present invention provides a process for producing trans-L-hydroxyproline, which comprises culturing a microorganism which is capable of decomposing amino acids other than trans-L-hydroxyproline but which is substantially incapable of decomposing trans-L-hydroxyproline in a culture medium containing collagen hydrolyzate, and recovering trans-L-hydroxyproline from the resulting culture.

DETAILED DESCRIPTION OF THE INVENTION

In accordance with the present invention, trans-L-hydroxyproline is produced by culturing, in a medium containing collagen hydrolyzate, a microorganism which can decompose amino acids other than trans-L-hydroxyproline. Any microorganism can be used in the present invention so far as it is capable of decomposing amino acids other than trans-L-hydroxyproline and does not substantially decompose trans-L-hydroxyproline. The amino acid decomposition in the present invention includes intracellular metabolism, assimilation and dissimilation. For example, microorganisms belonging to the genus *Proteus*, *Providencia*, *Deleya* or *Planococcus*, preferably, microorganisms belonging to the species *Proteus mirabilis*, *Providencia alcalifaciens*, *Deleya venusta* or *Planococcus citreus* may be used.

Examples of suitable preferred strains are *Proteus mirabilis* IFO 3849, *Providencia alcalifaciens* ATCC 9886, *Deleya venusta* ATCC 27125 and *Planococcus citreus* ATCC 14404. *Proteus mirabilis* IFO 3849 also has been deposited under the terms of the Budapest Treaty with the National Institute of Bioscience and Human-Technology 1-3, Higashi 1 chome, Tsukaba-shi Ibaraki-ken, 305, Agency of Industrial Science and Technology, Japan as FERM BP-4604. These strains are well known type strains that are readily available to the public. Other strains of these genera are equally employable and may be selected by known screening methods. The critical aspect of a suitable strain is the ability to decompose amino acids other than trans-L-hydroxyproline, such as aspartic acid, threonine, serine, asparagine, glutamic acid, proline, glycine, alanine, valine, cysteine, methionine, leucine, isoleucine, tyrosine, phenylalanine, histidine, lysine, arginine, hydroxylysine and α-aminobutyric acid, without decomposing trans-L-hydroxyproline.

Any of natural media and synthetic media can be used in the present invention so far as it contains collagen hydrolyzate either as the sole carbon and nitrogen sources, or in combination with other generally employed carbon sources, nitrogen sources, vitamins, etc. which can be assimilated by the microorganism used, and the microorganism which is capable of decomposing amino acids other than trans-L-hydroxyproline and does not substantially decompose trans-L-hydroxyproline can be efficiently cultured therein.

The amount of the collagen hydrolyzate in the culture medium should be adjusted so that the total amino acid concentration will be in the range of 10 to 300 g/l (trans-L-hydroxyproline: 1.5 to 45 g/l), preferably in the range of 40 to 200 g/l (trans-L-hydroxyproline: 6 to 30 g/l). The collagen hydrolyzate may also be added to the medium during the culturing.

Culturing may be carried out by any method suitable for the microorganism employed, but is generally carried out with stirring and aeration. The culturing temperature is usually in the range of 25° C. to 45° C., preferably 30° C. to 40° C. During the culturing, the pH is controlled to 7.5 to 8.0 by adding an inorganic acid such as hydrochloric or sulfuric acid, or an organic acid such as acetic acid.

Culturing is completed when the amino acids other than trans-L-hydroxyproline are decomposed, usually in 30 to 80 hours.

The cells are removed from the thus obtained culture by centrifugation, and trans-L-hydroxyproline is isolated from the supernatant by a purification method conventionally used in this field, such as column chromatography using an ion-exchange resin or crystallization.

Certain embodiments of the invention are illustrated in the following examples.

The collagen hydrolyzate used in the following examples and reference example was prepared in the following manner.

To 2 kg of oxhide, 5.1 l of 12 N sulfuric acid was added, and hydrolysis was carried out at 120° C. for 12 hours. After the reaction, 1 kg of calcium hydroxide and 8 l of water were added and the resulting suspension was filtered. Then, the filtrate was concentrated, and the concentrate was subjected to amino acid analysis using an amino acid analyzer. It was found that the concentrate contained 630 g/l amino acids, in which the content of trans-L-hydroxyproline, glycine and L-proline was 93 g/l, 158 g/l and 98 g/l, respectively. The concentrate was used as the collagen hydrolyzate.

EXAMPLE 1

Medium A comprising 10 g/l peptone, 7 g/l meat extract, 3 g/l sodium chloride and 5 g/l yeast extract (pH 7.0) was poured into test tubes in 5 ml portions and sterilized in an autoclave at 120° C. for 20 minutes to prepare a seed medium. One loopful of each of the microorganisms listed in Table 1 was inoculated into a seed medium and cultured at 30° C. for 24 hours with shaking. The resulting culture was used as a seed culture.

A medium comprising 40 g/l corn steep liquor and 150 ml/l collagen hydrolyzate (pH 7.5) was poured into test tubes in 5 ml portions and sterilized in an autoclave at 120° C. for 20 minutes to prepare a culture medium. Then, 0.5 ml of each seed culture was inoculated into a culture medium under sterile conditions, and cultured at 30° C. for hours with shaking. Five milliliters of each culture thus obtained was centrifuged at 1,000 rpm for 10 minutes to remove the cells, and the supernatant was analyzed for remaining amino acids with an amino acid analyzer.

Table 1 shows the trans-L-hydroxyproline content based on the total weight of amino acids in the culture and the residual rate of trans-L-hydroxyproline. These values were calculated as follows:

Content based upon total weight of amino acids =

$$\frac{\text{weight of trans-L-hydroxyproline contained in the culture}}{\text{total weight of the amino acids including trans-L-hydroxyproline contained in the culture}} \times 100\%$$

Residual Rate =

$$\frac{\text{weight of trans-L-hydroxyproline contained in the culture after completion of culturing}}{\text{weight of trans-L-hydroxyproline contained in the medium at the start of culturing}} \times 100\%$$

The trans-L-hydroxyproline content based on total weight of amino acids indicates the degree of decomposition of amino acids other than trans-L-hydroxyproline by the microorganism. If the microorganism completely decomposes amino acids contained in the medium other than trans-L-hydroxyproline, the value is 100%.

The residual rate of trans-L-hydroxyproline indicates the degree of decomposition of this substance in the medium by the microorganism. If there is no decomposition of trans-L-hydroxyproline by the microorganism, the value is 100%.

TABLE 1

| Strain | Trans-L-hydroxyproline content based on the total weight of amino acids (%) | Residual rate of trans-L-hydroxyproline (%) |
|---|---|---|
| *Proteus mirabilis* IFO 3849 | 89 | 99 |
| *Providencia alcalifaciens* ATCC 9886 | 60 | 98 |
| *Deleya venusta* ATCC 27125 | 67 | 99 |
| *Planococcus citreus* | 70 | 85 |

TABLE 1-continued

| Strain | Trans-L-hydroxyproline content based on the total weight of amino acids (%) | Residual rate of trans-L-hydroxyproline (%) |
|---|---|---|
| ATCC 14404 | | |

EXAMPLE 2

In this example, medium A having the same composition as described in Example 1 was poured into 1-liter Erlenmeyer flasks in 50 ml portions and sterilized in an autoclave at 120° C. for 15 minutes to prepare a seed medium. One loopful of *Proteus mirabilis* IFO 3849 was inoculated into the seed medium and cultured at 30° C. for 24 hours with shaking. The resulting culture was used as a seed culture.

Separately, 750 ml of a culture medium comprising 30 g of corn steep liquor and 160 ml of collagen hydrolyzate (pH 7.5) was poured into a 2-liter jar fermenter and sterilized in an autoclave at 120° C. for 30 minutes. Then, 50 ml of the seed culture was inoculated into the culture medium under sterile conditions, and cultured at 37° C. for 30 hours with stirring and aeration (rotation: 1,000 rpm, aeration: 1 vvm). During culturing, the culture medium was adjusted to pH 8.0 by addition of 5N sulfuric acid. The residual rate of trans-L-hydroxyproline was 94%, and its content based on the total weight of amino acids in the culture was 94%.

The culture thus obtained (800 ml) was centrifuged at 10,000 rpm for 10 minutes to remove the cells, and the supernatant was passed through a column packed with 200 ml of an ion-exchange resin [Diaion SK-1B (H+ type); a product of Mitsubishi Kasei Corporation] to adsorb amino acids on the resin. The resin was then washed with water, and trans-L-hydroxyproline was eluted with 0.2N aqueous ammonia. The residual rate of trans-L-hydroxyproline was 90% and its content based on the total weight of amino acids was 96%.

The eluate was then concentrated under reduced pressure, followed by addition of methanol to precipitate crystals. Recrystallization from water gave 10.5 g of trans-L-hydroxyproline (purity: 99.9%).

EXAMPLE 3

In this example, the same seed culture and the same culture medium as in Example 2 were used. The seed culture (50 ml) was inoculated into the culture medium under sterile conditions, and culturing with stirring and aeration was carried out at 37° C. in the same manner as in Example 2. Twenty hours after the start of culturing, 160 ml of collagen hydrolyzate was added to the medium. Culturing was completed 60 hours after the start. The residual rate of trans-L-hydroxyproline was 93% and its content based on the total weight of amino acids in the culture was 90%.

The culture thus obtained was subjected to purification in the same manner as in Example 2, whereby 20.8 g of trans-L-hydroxyproline (purity: 99.0%) was obtained.

In the present invention, microorganisms which are substantially incapable of decomposing trans-L-hydroxyproline can be used; for example, the residual rate is 85% with *Planococcus citreus* ATCC 14404 as shown in Table 1. Thus, a residual rate of less than 100% is acceptable for the present invention as long as the microorganism has the ability to decompose to a substantially greater extent the other amino acids in the medium as is reflected by the value for the content based upon total weight of amino acids after culturing.

REFERENCE EXAMPLE

In this example, 200 ml of collagen hydrolyzate was diluted five-fold with water and passed through a column packed with 200 ml of an ion-exchange resin [Diaion SK-1B (H+ type)] to adsorb amino acids on the resin. The ion-exchange resin was then washed with water, and trans-L-hydroxyproline was eluted with 0.2N aqueous ammonia. The residual rate of trans-L-hydroxyproline was 76% and its content based on the total weight of amino acids was 30%.

The eluate was then passed through a column packed with 200 ml of a strongly basic ion-exchange resin [PA-412 (OH− type); a product of Mitsubishi Kasei Corporation]. The ion-exchange resin was washed with water, and trans-L-hydroxyproline was eluted with a 0.075N hydrochloric acid. The residual rate of trans-L-hydroxyproline was 74% and its content based on the total weight of amino acids was 61%. The eluate was then passed through a column packed with 200 ml of an ion-exchange resin [Diaion SK-1B (H+ type)]. The ion-exchange resin was washed with water, and trans-L-hydroxyproline was eluted with 0.2N aqueous ammonia. The residual rate of trans-L-hydroxyproline was 77% and its content based on the total weight of amino acids was 82%.

The final yield of trans-L-hydroxyproline after the above three steps of chromatography was 43%, and its content based on the total weight of amino acids was 82%.

What is claimed is:

1. A process for producing trans-L-hydroxyproline, which comprises culturing a microorganism selected from the group consisting of *Proteus mirabilis* IFO 3849 (FERM BP-4604), *Providencia alcalifaciens* ATCC 9886, *Delaya venusta* ATCC 27125 and *Planococcous citreus* ATCC 14404, the microorganism decomposes amino acids comprising alanine, arginine, aspartic acid, cysteine, glutamic acid, glycine, lysine, proline, serine, threonine, valine and tyrosine, but not trans-L-hydroxyproline, in a culture medium containing collagen hydrolyzate until amino acids other than trans-L-hydroxyproline in the culture medium are decomposed, and thereafter recovering said trans-L-hydroxyproline from the resulting culture.

* * * * *